United States Patent [19]

Demarne et al.

[11] Patent Number: 4,946,868

[45] Date of Patent: Aug. 7, 1990

[54] ANTIMICROBIAL COMPOSITIONS CONTAINING BENZOIC ACID DERIVATIVES FOR USE AS DISINFECTANTS, DRUGS OR PRESERVATIVE AGENTS

[75] Inventors: Henri Demarne; Robèrt Filhol; Madeleine Mosse, all of Montpellier, France

[73] Assignee: Sanofi, Paris, France

[21] Appl. No.: 640,107

[22] Filed: Aug. 13, 1984

[30] Foreign Application Priority Data

Aug. 18, 1983 [FR] France .................................. 83 13445

[51] Int. Cl.$^5$ ........................ A61K 7/06; A61K 7/48; A61K 31/185
[52] U.S. Cl. .................................... 514/544; 252/106; 252/107; 424/70; 426/72; 426/73; 426/662; 514/844; 514/846; 514/848; 514/861; 514/863; 514/886; 514/887; 514/969
[58] Field of Search ......................... 424/308; 514/544

[56] References Cited

U.S. PATENT DOCUMENTS 4,016,186  4/1977  Kondo et al. ...................... 424/308

FOREIGN PATENT DOCUMENTS 2241296  2/1978  France ............................ 514/544
2272647  3/1979  France ............................ 514/544
1050136  1/1976  United Kingdom ................ 514/544

OTHER PUBLICATIONS

Mizuo et al., Chem. Abst. 84:173809h, (1975).
Makuchi et al., Chem. Abst. 84:173810b, (1975).
Fujita et al., Chem. Abst. 84:173811c, (1975).
Takeda et al., Chem. Abst. 80:59705p, (1973).
Milko et al., Chem. Abst. 80:124576p, (1973).

*Primary Examiner*—Dale R. Ore
*Attorney, Agent, or Firm*—Stevens, Davis, Miller & Mosher

[57] ABSTRACT

The invention concerns compositions with antimicrobial activity.

These compositions contain a benzoic acid derivative with the formula:

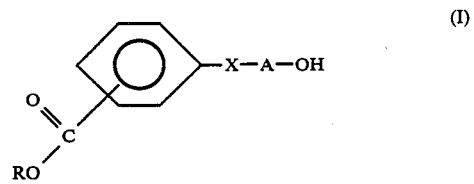

in which:
A represents a straight or branched alkyl chain with 3 to 4 carbon atoms,
X represents the oxygen atom or a direct bond,
R represents hydrogen or an alkyl group with 2 to 6 carbon atoms, possibly substituted by an alcohol function and a salt of such a derivative.

Applications: drugs, disinfectants and preservative agents.

2 Claims, No Drawings

ANTIMICROBIAL COMPOSITIONS CONTAINING BENZOIC ACID DERIVATIVES FOR USE AS DISINFECTANTS, DRUGS OR PRESERVATIVE AGENTS

This invention concerns compositions for antiseptic use containing benzoic acid derivatives with the general formula:

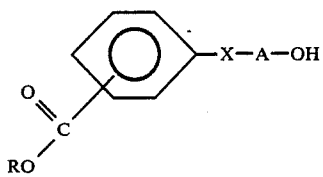
(I)

in which:
- A represents a straight or branched alkyl chain with 3 to 4 carbon atoms,
- X represents the oxygen atom or a direct bond,
- R represents hydrogen or an alkyl group with 2 to 6 carbon atoms, possibly substituted by an alcohol function.

This invention also concerns the use, in compositions for antiseptic use, of suitable salts of (I).

These compounds display antimicrobial activity, they can be used in particular as antiseptic drugs for human or veterinary use, or as disinfectants on inert surfaces. They can also be used as preservative agents.

Compounds (I) in which X represents a direct bond can be prepared according to the method described in J.Med.Chem., 1983, Vol. 26, pp. 335–341 from a toluic acid.

They can also be prepared from nitrophenylalkanols or nitrophenoxyalkanols (IV). By catalytic hydrogenation of (IV), derivatives of the corresponding aniline (V) are obtained, and diazoniums are obtained by the addition of sodium nitrite in acidic medium. The action of cuprous cyanide, by Sandmeyer's reaction, leads to the derivatives of benzonitrile (VI). Finally, compounds (I) are synthetized by reactions that are well-known, and possibly converted to a suitable salt.

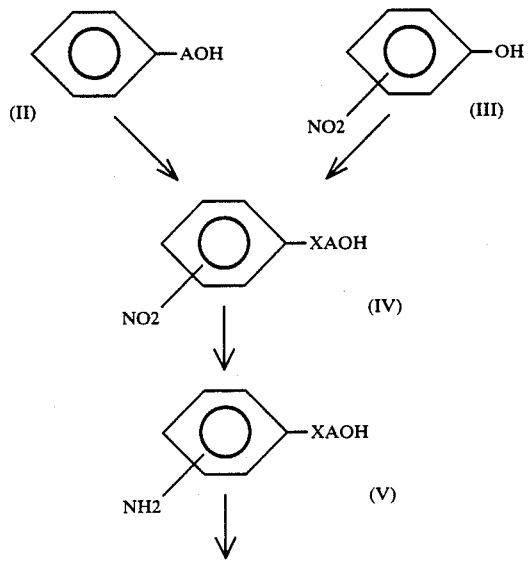

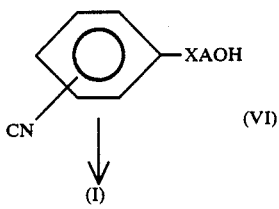

If X represents a direct bond, nitrophenylalkanol (IV) is prepared from phenylalkanol (II). The hydroxyl group is previously protected by acetylation using acetyl chloride. After nitration by fuming nitric acid, the alcohol is liberated by the action of hydrochloric methanol.

The phenylalkanols (II) are accessible commercially if linear alcohols are involved. If not, they can be prepared by various methods. For example, secondary phenylalkanols are prepared from phenylacetaldehyde by the action of a magnesium derivative followed by hydrolysis:

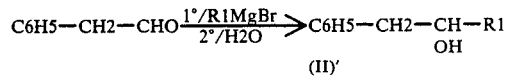

R1   alkyl with 1 to 8 carbons

Primary branched phenylalkanols are obtained from benzyl cyanide:

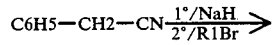

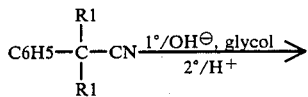

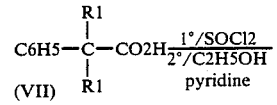

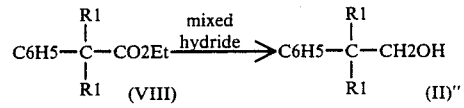

After causing sodium hydride to react in anhydrous medium, an alkyl halogenide, such as the bromide, can be added to obtain a symmetrical dialkylated phenyl acetonitrile. The conversion of this compound to the acid is carried out by the action of a base in alcoholic medium, followed by acidification.

The action of thionyl chloride and then ethyl alcohol in anhydrous medium in the presence of a catalyst, such as pyridine or dimethylaminopyridine, serves to obtain the ethyl ester (VII). The corresponding alcohol (II)" is then prepared by reduction using a mixed hydride in an anhydrous solvent.

If X represents oxygen, nitrophenoxyalkanol (IV) is prepared from nitrophenol (III). The action of an alkyl halogenide on (III) in basic medium serves to obtain a nitrophenoxyalkyl halogenide (IX). This product is acetylated in acidic medium and then (IV) is liberated by saponification:

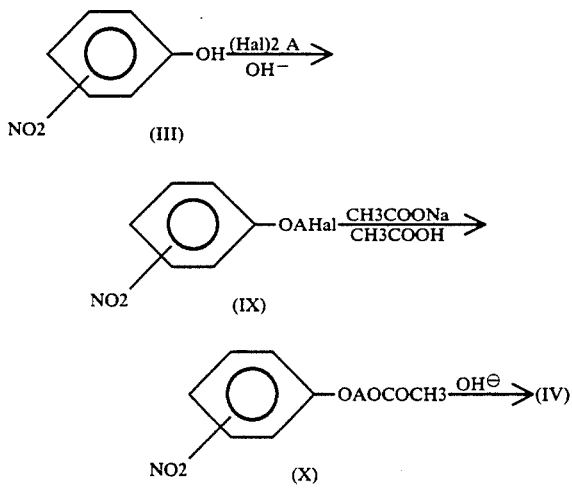

In all cases, compounds (I) where R=alkyl or hydroxyalkyl are obtained from compounds (I) where R=H by standard esterification processes, and particularly by the action of R—OH alcohol on the acid in the presence of a strong acid as a catalyst, or by the action of an R Hal halogenide on the sodium salt of the acid.

The following examples illustrate the invention, without limiting it. If the product obtained is in oil form, it is characterized by its nuclear magnetic resonance (NMR) spectrum. The latter is recorded at 60 MHz in deuterochloroform, using hexamethyldisiloxane as an internal standard.

To describe the spectrum, the following abbreviations are employed:
S: single.
D: doublet.
T: triplet.
Q: quadruplet.
M: multiplet.
J: coupling constant.

EXAMPLE 1

(hydroxy-3 propyl)-4 benzoic acid: SR 41323

(a) (Nitro-4 phenyl)-3 propanol-1

95 ml of acetyl chloride are added to 171.5 g of phenyl-3 propanol-1, in 1 hour with agitation. The mixture is heated for 2 hours under reflux, and the hydrochloric acid liberated and excess acetyl chloride are eliminated. When the reaction medium returns to ambient temperature, it is transferred drop by drop, with mixing, to 800 ml of fuming nitric acid (d=1.49) cooled to −25° C. The addition lasts one hour, during which the temperature is kept between −15° and −20° C. The mixture is then transferred to 1.5 l of water containing crushed ice, and extracted three times with ether, washed three times with water, three times with a 10% sodium carbonate solution, and then three times with water. The ether phases are dried on magnesium sulfate and evaporated to dryness under reduced pressure. The residue is taken up with 800 ml of methanol, and hydrochloric acid gas caused to bubble for 1 hour at 0° C., and the mixture then heated for 14 hours under reflux. After evaporation of the solvent, the residue is taken up in the water/ether mixture, the aqueous phase settled, washed twice with water, three times with a saturated sodium bicarbonate solution, and then three times with water. The ether phase is then dried on magnesium sulfate, and then evaporated to dryness under reduced pressure.

259 g of orange colored oil are obtained, and purified by chromatography on 3 kg of silica gel in chloroform. 218 g of orange colored oil are recovered. Yield 95%.

(b) (Hydroxy-3 propyl)-4 aniline 218 g of (nitro-4 phenyl)-3 propanol-1 are dissolved in 500 ml of methanol, and 10 g of 10% palladium on coal, previously wetted with 10 ml of water, are added. Hydrogenation takes place under 40 bar pressure and with agitation, and lasts 1 hour 30 minutes. The mixture is then filtered on celite, rinsed with methanol, evaporated to dryness under reduced pressure to obtain 168 g of a brown oil. This is purified by three successive chromatographies on a total of 6 kg of alumina, using dichloromethane as eluent. 49.2 g of a pale brown powder are obtained. Fc=43° to 45° C. Yield 27%.

(c) (Hydroxy-3 propyl)-4 benzonitrile 49.07 g of product previously obtained are transferred to 87 ml of concentrated hydrochloric acid containing 400 g of crushed ice. Keeping the temperature between 0° and 5° C., a solution of 23.15 g of sodium nitrite in 80 ml of water is added drop by drop, and then, after 10 minutes of agitation, the mixture is neutralized with 300 ml of 10% sodium carbonate solution.

A solution of cuprous cyanide is prepared separately. 40.35 g of cuprous chloride are placed in suspension in 150 ml of water, and a solution of 54 g of sodium cyanide in 80 ml of water is added. The liberation of heat is observed, the cuprous chloride is dissolved, and the solution loses its color. To this solution, cooled to 0° C. and to which 200 ml of benzene are added, the diazonium solution cooled to 0° C. is added drop by drop, over a period of 40 minutes, with violent agitation. After 40 minutes of additional agitation, it is allowed to return to ambient temperature, with agitation, and then heated to 50° C. without agitating and returned to ambient temperature.

It is extracted three times with ether, washed twice with water, and then with a saturated sodium chloride solution. The ether phases are dried over magnesium sulfate and evapored to dryness under reduced pressure. 51 g of a dark brown oil are obtained. This is purified by chromatography on 1500 g of silica gel, the column is prepared in toluene, and the eluent is a toluene/ether mixture (9/1 v/v). 41.6 g of pure product are obtained in the form of a red oil. Yield 79%.

The product is characterized by its NMR spectrum:
2H between 1.7 and 2.2 ppm (M, —CH2—CH2—CH2—OH). 1H at 2.4 ppm (S, —OH). 2H at 2.8 ppm (T, J=7 Hz, CN—C6H4—CH2—CH2—). 2H at 3.6 ppm (T, J=6 Hz, —CH2—CH2—OH). 2H at 7.3 ppm (D, J=9 Hz, H ortho CH2). 2H at 7.6 ppm (D, J=9 Hz, H ortho CN).

(d) SR 41323

41 g of the previous product are dissolved in 150 ml of 95% alcohol, 15 g of caustic soda are added, and the mixture heated under reflux for 17 hours with agitation. After cooling, it is evaporated to dryness under reduced pressure, and the residue taken up in water and acidified to a pH of approximately 1 by concentrated hydrochloric acid. It is extracted twice with ether, washed twice with water, and then with a saturated sodium chloride solution. The ether phases are then dried over magnesium sulfate and evaporated to dryness under reduced pressure. The yellow crystals obtained are recrystallized in an ether/hexane mixture.

33.7 g of a cream colored powder are obtained. Melting point Fc=138° to 141° C.

EXAMPLE 2

Ethyl (hydroxy-3 propyl)-4 benzoate: SR 41324

13.5 g of the previously obtained product (SR 41323) are dissolved in 200 ml of absolute ethanol, and 6 ml of thionyl chloride are added drop by drop, with agitation. When the reaction medium returns to ambient temperature, it is heated under reflux for 6 hours with agitation, and then allowed to stand overnight at ambient temperature. The solvents are evaporated under reduced pressure, and the mixture extracted three times with ether, washed twice with a saturated sodium bicarbonate solution, twice with water, and then with a saturated sodium chloride solution. The ether phases are then dried over magnesium sulfate and evaporated to dryness under reduced pressure.

15.43 g are obtained, corresponding to the final product, characterized by its NMR spectrum:

3H at 1.3 ppm (T, J=7 Hz, —CO2—CH2—CH3). 3H between 1.5 and 2.2 ppm (massive, HO—CH2—CH2—CH2—). 2H at 2.7 ppm (T, J=7 Hz, HO—CH2—CH2—C6H4). 2H at 3.6 ppm (T, J=6 Hz, HO—CH2—CH2—CH2—). 2H at 4.3 ppm (Q, J=7 Hz, —CO2—CH2—CH3). 2H at 7.2 ppm (D, J=9 Hz, H ortho CH2). 2H at 7.9 ppm (D, J=9 Hz, H ortho CO2).

EXAMPLE 3

(Hydroxy-2 butyl)-4 benzoic acid: CM 41074

(a) Phenyl-1 butanol-2

A solution of 7.5 ml of ethyl bromide in 50 ml of anhydrous ether is added to 2.92 g of magnesium turnings, under nitrogen, drop by drop, at a rate sufficient to maintain slight reflux. Still under nitrogen, it is agitated for 2 hours at ambient temperature, and then 9.4 ml of phenylacetaldehyde are added drop by drop, and the mixture left for 2 hours at ambient temperature with agitation.

It is then decomposed on 200 ml of 20% ammonium chloride cooled to 0° C., and extracted three times with ether. After three washings with water, the ether phases are dried over magnesium sulfate and evaporated to dryness under reduced pressure. 12.2 g of a slightly yellowish oil are obtained.

(b) CM 41074

By then using the processes described in Example 1, CM 41074 is prepared, and recrystallized in an ether/hexane mixture. Fc=103° to 106° C.

EXAMPLE 4

Ethyl (hydroxy-2 butyl)-4 benzoate: CM 41075

This product is prepared from acid CM 41074, and is characterized by its NMR spectrum:

3H at 0.9 ppm (T, J=7 Hz, CH3—CH2—CH(OH)—CH2—). 6H between 1.1 and 1.7 ppm (massive, CH3—CH2—CH(OH), —CO2—CH2—CH3). 2H between 2.6 and 2.9 ppm (M, CH(OH)—CH2—C6H4—). 1H between 3.5 and 3.9 ppm (M, —CH2—CH(OH)—CH2). 2H at 4.3 ppm (Q, J=7 Hz, —CO2—CH2—CH3). 2H at 7.3 ppm (D, J=9 Hz, H ortho CH2). 2H at 8 ppm (D, J=9 Hz, H ortho CO2).

EXAMPLE 5

(Hydroxy-4 butyloxy)-4 benzoic acid, CM 40841

(a) (Nitro-4 phenoxy)-1, bromo-4 butane 83 ml of dibromo-1,4 butane are added to a solution of nitro-4 phenol in 275 ml of water, and then, drop by drop, 49.5 ml of 10N Sodium hydroxide with agitation. The mixture is heated under reflux with agitation for 24 hours.

After cooling, it is extracted three times with ether, washed six times with normal caustic soda, and then three times with water. The ether phases are dried over sodium sulfate and evaporated, and the insoluble material filtered. The filtrate is evaporated to dryness and the residue drawn under vacuum (0.05 mmHg). After grinding in hexane, crystals are obtained, filtered, washed with hexane and dried under vacuum in the desiccator.

75 g of a pasty cream colored product are obtained. Yield 55%.

(b) (Nitro-4 phenoxy)-1 acetyloxy-4 butane 75 g of the previous product are dissolved in 80 ml of glacial acetic acid, 45 g of anhydrous sodium acetate added, and the mixture heated under reflux for 15 minutes with agitation. The reaction mixture is transferred to 1 liter of iced water containing 500 ml of ether, and neutralized to pH 7.5 with solid sodium carbonate. After three extractions with ether and three washings with water, the ether phases are dried over magnesium sulfate and evaporated to dryness, and the residue is drawn out under vacuum.

m=70 g of an orange colored oil are obtained. Yield 100%.

(c) (Nitro-4 phenoxy)-1 butanol-4

70 g of the previous product are dissolved in 300 ml of methanol, 30 ml of 10N Sodium hydroxide are added, and the mixture heated under reflux for 4 hours with agitation. After evaporating the methanol, the residue is taken up in a water/ether mixture, extracted three times with ether, washed three times with a saturated sodium chloride solution.

The ether phases are then dried over magnesium sulfate and evaporated to dryness. The crystals formed are ground in hexane, filtered, washed with hexane and dried under vacuum in the desiccator.

48.8 g of slightly yellowish crystals are obtained. Fc=53° to 55° C.

(d) CM 40841

Proceeding as in Example 1, the following compounds are then prepared:

(Hydroxy-4 butyloxy)-4 aniline, Fc=56° to 58° C., (Hydroxy-4 butyloxy)-4 benzonitrile, Fc=54° to 58° C., CM 40841, Fc=143° to 145° C. after recrystallization in ether.

EXAMPLE 6

(Hydroxy-4 butyl)-2 benzoic acid, SR 42452

140 ml of 1.6 mole solution of butyllithium in hexane are added to a solution of 22.6 g of diisopropylamine in 200 ml of tetrahydrofuran and 28 ml of hexamethylphosphoramide, drop by drop, at 0° C. The suspension of 15.1 g of methyl-2 benzoic acid in 50 ml of tetrahydrofuran is then added at 0° C., and the mixture is agitated for 1 hour, while keeping the temperature at 0° C.

The temperature is lowered to −5° C. and 29.7 g of (iodo-3 propoxyl)-2 tetrahydro 2H pyran are added drop by drop. The mixture is agitated for 1 hour at 0° C., water is then added, and the mixture extracted with ether. The aqueous phase is separated, acidified and extracted with ether. The organic phase is dried over sodium sulfate and the solvent evaporated under vacuum.

The oily residue is dissolved in methanol. 120 ml of aqueous solution of 2N hydrochloric acid are added, and the mixture agitated for 10 minutes. The solvents are evaporated under vacuum, the residue taken up in water and extracted with ether. The ether solution is washed twice with water, dried over sodium sulfate and the solvents evaporated under vacuum.

The residue is chromatographed on silica, using dichlorethane as eluent.

5 g of the final product are obtained. Fc: 57° to 59° C.

By using similar preparation processes, the compounds are prepared, according to the invention, described in Table 1 below. They are characterized by their NMR spectrum or their melting point, measured after recrystallization in an ethanol/hexane mixture, or in hexane only for SR 41614.

TABLE 1

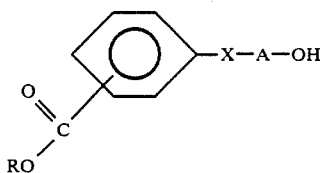

(I)

| product No. and position | X | A-OH | R | prepared according to Example | melting point (°C.) |
|---|---|---|---|---|---|
| SR 41576 p | — | (CH2)4OH | H | 1 | 75 to 80 |
| CM 40714 p | 0 | (CH2)3OH | H | 5 | 129 to 131 |
| SR 41577 m | 0 | (CH2)4OH | H | 5 | 105 to 107 |
| SR 41614 o | 0 | (CH2)4OH | H | 5 | 51 to 53 |
| SR 41462 p | — | (CH2)4OH | C2H5 | 2 | NMR |
| CM 40715 p | 0 | (CH2)3OH | C2H5 | 5 | NMR |
| CM 40842 p | 0 | (CH2)4OH | C2H5 | 5 | NMR |
| SR 42410 p | — | (CH2)4OH | C2H4OH | 1 | 57 to 60 |
| SR 42791 o | — | (CH2)4OH | C2H5 | 2 | NMR |
| SR 42900 m | 0 | (CH2)4OH | C2H5 | 2 | NMR |
| SR 42913 p | — | —C(CH3)2CH2OH | C2H5 | 2 | NMR |

NMR spectra of products according to the invention:

SR 41462

3H at 1.3 ppm (T, J=7 Hz, —CO2—CH2—CH3). 4H between 1.4 and 1.8 ppm (massive, HO—CH2—CH2—CH2—CH2—). 1H at 1.9 ppm (S, HO—). 2H at 2.6 ppm (T, J=7 Hz, —CH2—CH2—CH2—CH2—C6H4). 2H at 3.6 ppm (T, J=6 Hz, HO—CH2—CH2—CH2—CH2—). 2H at 4.3 ppm (Q, J=7 Hz, —CO2—CH2—CH3). 2H at 7.3 ppm (D, J=9 Hz, H ortho CH2). 2H at 8 ppm (D, J=9 Hz, H ortho CO2).

CM 40715

3H at 1.3 ppm (T, J=7 Hz, —CO2—CH2—CH3). 4H between 1.5 and 2.2 ppm (massive, Ho—CH2—CH2—CH2—O—). 3H between 3.5 and 3.9 ppm (massive, —CH2—CH2—O—C6H4, HO). 2H at 4.1 ppm (T, J=6 Hz, HO—CH2—CH2—). 2H at 4.3 ppm (Q, J=7 Hz, —CO2—CH2—CH3). 2H at 6.9 ppm (D, J=9 Hz, H meta CO2). 2H at 8 ppm (D, J=9 Hz, H ortho CO2).

CM 40842

3H at 1.3 ppm (T, J=7 Hz, —CO2—CH2—CH3). 2H between 1.7 and 2.3 ppm (M, —CH2—CH2—CH2—O—C6H4—). 2H at 3.8 ppm (T, J=6 Hz, —CH2—CH2—O—C6H4). 2H at 4.1 ppm (T, J=7 Hz, HO—CH2—CH2—CH2—). 2H at 4.3 ppm (Q, J=7 Hz, —CO2—CH2—CH3). 2H at 6.9 ppm (D, J=9 Hz, H meta CO2). 2H at 8 ppm (D, J=9 Hz, H ortho CO2).

CM 42791

3H at 1.3 ppm (T, J=7 Hz, CO2CH2CH3). 4H between 1.35 and 1.85 ppm (M, HO—CH2—CH2—CH2—CH2—). 1H at 1.95 ppm (S, OH). 2H at 2.9 ppm (T, J=6 Hz, CH2—CH2—C6H4). 2H at 3.62 ppm (T, J=6 Hz, HOCH2—CH2). 2H at 4.27 ppm (Q, J=7 Hz, CO2CH2CH3). 3H between 7 and 7.6 ppm (M, H aromatic, meta and para CO2). 1H at 7.85 ppm (D of D, J1=8 Hz, J2=2 Hz, H ortho CO2).

CM 42900

3H at 1.3 ppm (T, J=7 Hz, CO2CH2CH3). 5H between 1.5 and 2.1 ppm (M, HO—CH2—CH2—CH2—CH2—). 2H at 3.68 ppm (T, J=6 Hz, HO—CH2CH2). 2H at 3.98 ppm (T, J=6 Hz, O—CH2CH2—). 2H at 4.27 ppm (Q, J=7 Hz, CO2CH2CH3). 4H between 6.83 and 7.8 ppm (M, H aromatic).

CM 42913

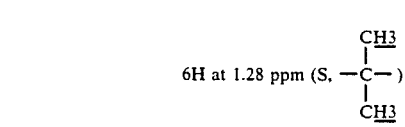

6H at 1.28 ppm (S, —C(CH3)(CH3)—)

3H at 1.3 ppm (T, J=7 Hz, CO2CH2CH3). 1H at 1.53 ppm (broad S, OH). 2H at 3.57 ppm (S, CH2OH). 2H at 4.29 ppm (Q, J=7 Hz, CO2CH2CH3).

| 2H at 7.4 ppm | system AA', BB' | 2H aromatics meta CO2 |
| 2H at 7.9 ppm | | 2H aromatics ortho CO2 |

The bactericidal activity of the products according to the invention has been analyzed on different strains by the method described below.

A bacterial inoculum is placed in contact with different dilutions of the product to be tested, during a limited time interval. At the end of contact, one aliquot of the baterial suspension/product mixture is deposited on the surface of an agar culture medium containing a substance neutralizing the product's antibacterial action.

The bactericidal concentration selected is the minimum concentration of the product from which the bacteria no longer grow. This concentration is expressed in µg/ml.

The bacterial strains selected for the study are:
(1) *Escherichia coli* CNCM 54125.
(2) *Klebsiella pneumoniae* R030 encapsulated.
(3) *Pseudomonas aeruginosa* CNCM A22.
(4) *Streptococcus faecalis* CNCM 5855.
(5) *Staphylococcus aureus* CNCM 53154.

The second is supported on Worgel Fergusson medium, and the others on Tryptic Soy Agar-Difco (TSA).

After 24 hours of culture at 37° C., the microbial growth is collected using glass spheres and 10 ml of diluent containing 1 g of tryptone and 8.5 g of sodium chloride in 1000 ml of distilled water. The suspension formed is agitated, and the percentage light transmission at 620 nm is measured on the spectrophotometer:
strain 1: 70%
strain 2: 80%
strain 3: 70%
strain 4: 60%
strain 5: 60%

The bacterial inoculum corresponds to a 1/20 suspension of this bacterial suspension.

Plates with cups receive different dilutions of the product to be analyzed. These dilutions are placed in contact with the different bacterial suspensions using a Steers type multiple site inoculator. After 20 minutes of contact, aliquots are transferred using this inoculator to the surface of an agar medium (TSA) placed in Petri dishes, containing an activity neutralizer, namely 20 g of lubrol W, 2.5 g of Tween 80 and 2.5 g of sodium thiosulfate in 1000 ml of TSA (Difco). A reference standard of the neutralizer efficiency is prepared for each product tested, by depositing an aliquot of the dilution of the product to be analyzed on the surface of the culture medium. The corresponding inoculum is deposited at the same place. A reference inoculum is prepared on agar medium with and without neutralizer. The reading is taken after 48 hours of incubation at 37° C.

The results are given in Table 2 below.

TABLE 2

| product No. | Minimum bactericidal concentration (MBC) in µg/ml bacteral strain | | | | |
|---|---|---|---|---|---|
| | 1 | 2 | 3 | 5 | 6 |
| SR 41323 | 1500 | 500 | 500 | 3000 | 1500 |
| SR 41576 | 500 | 500 | 100 | 1000 | 500 |
| CM 41074 | 2000 | 500 | 1000 | 2000 | 2000 |
| CM 40714 | 1000 | 1000 | 500 | 1000 | 2000 |
| CM 40841 | 2000 | 1000 | 500 | 2000 | 1000 |
| SR 41577 | 500 | 200 | 200 | 1000 | 500 |

TABLE 2-continued

| product No. | Minimum bactericidal concentration (MBC) in µg/ml bacteral strain | | | | |
|---|---|---|---|---|---|
| | 1 | 2 | 3 | 5 | 6 |
| SR 41614 | 500 | 500 | 200 | 1000 | 500 |
| CM 40715 | 1000 | 2000 | 500 | 2000 | 2000 |
| CM 40842 | 1000 | 1000 | 500 | 2000 | 2000 |
| SR 41462 | 500 | 500 | 500 | 800 | 500 |
| CM 41075 | 500 | 1000 | 1000 | 2000 | 2000 |
| SR 42452 | 1000 | 1000 | 500 | 1000 | 1000 |
| SR 42900 | 1000 | 500 | 500 | 1000 | 500 |
| SR 41324 | 600 | 600 | 600 | 2500 | 2000 |
| SR 42791 | 1500 | 1000 | 500 | 1500 | 1500 |
| SR 42913 | 500 | 500 | 100 | 1000 | 500 |

The results show that the products according to the invention display a broad spectrum of activity on the bacterial strains tested.

The antifungal activity of the products according to the invention was also determined by the method of seriated dilutions in agar medium.

Mother solutions of the different products are prepared with 20% tetraglycol. Using these mother solutions, a range of dilutions is prepared in a geometric progression at the rate of ½. 2 ml of each of these dilutions are transferred to the Petri dishes, and 1.8 ml of 'Sabouraud Dextrose Agar' agar medium (Difco) are added.

The inoculum for yeasts consists of a 1/20 dilution of a 48-hour culture at 27° C. in Sabouraud liquid medium. For dermatophytes and contaminants, the inoculum is prepared by the collection of a culture in Sabouraud agar medium, using 5 ml of liquid Sabouraud medium.

The inoculum is deposited on the surface of the Petri dishes using a multiple site inoculator. The reading is taken after 48 hours of incubation at 27° C. for yeasts, after 7 days of incubation at 27° C. for dermatophytes, and after 4 days of incubation at 27° C. for contaminants. The minimum inhibiting concentration or MIC, expressed in µg/ml, represents the lowest concentration at which no growth occurs.

Table 3 gives the results obtained with different products according to the invention.

Experiments were performed with 22 yeast strains, 18 dermatophyte strains, and 18 contaminant strains. The results (MIC in µg/ml) represent the extreme values obtained for each category.

TABLE 3

| product No. | Antifungal activity | | |
|---|---|---|---|
| | yeasts | dermatophytes | contaminants |
| SR 41462 | 300 to 750 | 9 to 38 | 300 to 750 |
| SR 41577 | 1500 | 150 | 1500 |
| CM 41075 | 500 to 1000 | 62.5 | 250 to 1000 |
| CM 40715 | 500 to 1000 | 62.5 to 125 | 500 to 1000 |

These results show that the products according to the invention exhibit good activity with the fungi analyzed.

The tolerance of the products according to the invention was analyzed in the guinea-pig. The animals were shaved on both sides of the median line of the back, and shaved again every two days. Batches of six animals received 0.2 ml of an aqueous or alcoholic solution of the product according to the invention, on the shaved zone. When the products were in alcohol solution, a batch of control animals received the alcohol on one side.

To analyze the preliminary cutaneous tolerance, the treatment was applied once daily, six days out of seven, for three weeks. Cutaneous observations covered the presence of erythema, cutaneous eruption or hyperkeratosis, of which the intensity was graduated in accordance with a predetermined scale.

The skin sensitization test was performed on the same animals after 2 weeks of rest. The treatment last 1 week, and was identical to the above. Evaluation was carried out with the same criteria and according to the same scale as the one used for local tolerance.

It was also determined whether the products according to the invention displayed a phototoxic or photoallergic effect in the guinea-pig. The technique used was that of J. Unkovic, G. Mazué and J. Girard, in Sciences et Techniques de l'Animal de Laboratoire, Vol. 8 (3) 149-160 (1983). It was an adaptation of the techniques described by L. C. Harber et al, Arch.Dermatol., 1967, Vol. 96, pp. 646-656, and L. J. Vinson et al, J.Soc.-Cosm.Chem., 1966, Vol. 17, pp. 123-130.

None of the products analyzed displayed poor tolerance, sensitizing effect or phototoxic or photoallergic effect in the guinea-pig.

An evaluation of acute oral toxicity was performed in the mouse. This analysis was conducted on male mice of strain CD1 from the Charles River breeding farm. Each batch consisted of five animals with a body weight ranging from 24 to 30 g, kept in the same cage.

The animals were starved for 6 hours before treatment. For each analysis, the product, placed in suspension in a solution of 10% gum arabic, was administered by forcible feeding using an oesophageal probe.

The regimen was again distributed to the animals 4 hours after forcible feeding, and the animals were kept under observation for 14 days after administration.

During this period, the mortality rate was noted in each of the experimental batches, and, whenever possible, the lethal dose 50 (LD 50) was determined using the Litchfield and Wilcoxon method.

The following results, expressed in mg of substance tested per kg of body weight, were obtained:

SR 41323: LD>50,000.
SR 41576: LD between 4000 and 5000.

The compounds according to the invention display an interesting level of activity, which compares favorably with that of the main families of antiseptics used in practice.

In addition, the products according to the invention display uniform activity to the different bacterial species analyzed. Moreover, they exhibit low toxicity, have displayed good tolerance, and are devoid of any sensitizing effect, phototoxic or photoallergic effect.

Accordingly, the products according to the invention can serve for many applications as antiseptics, preservatives and disinfectants.

In particular, they can be used as antiseptics in preparations for therapeutic purposes, for example for the treatment of impetigo, acne, infected dermatoses, infected open wounds, closed infections such as boils, whitlows, impetiginous scabies etc. Use for preventive purposes can also be considered, for example for the preparation of the surgical area, the preparation of the hands of the surgeon or of the hospital personnel.

In veterinary applications, the products according to the invention can be used as antiseptics (for example in the prevention of mammitis) or as disinfectants (disinfection of stables, equipment) and also in the agri-foodstuffs field.

Finally, their good tolerance and low toxicity allows their use as preservative agents, not only in drugs and cosmetics, but also in the agri-foodstuffs field.

Different galenic formulations of the products according to the invention can be prepared in accordance with their intended application.

EXAMPLE 7

Antiseptic alcohol solution

SR 41462: 0.5 g
alkyldimethylcarboxymethylamine (30% solution): 0.5 g.
condensate of ethylene oxide and propylene glycol L62: 1 g.
lactic acid or sodium hydroxide added to pH 6.5.
70% ethyl alcohol added for a total of: 100 g.

EXAMPLE 8

A product according to the invention can be used as a shampoo preservative potassium and amino acid palmitate: 20 g.
sodium alkylsulfates: 2 g.
copra diethanolamide: 5 g.
linolyl acetate: 0.200 g.
CM 41075: 0.150 g.
sodium hydroxide added to pH 7.
purified water added to a total of: 100 g.

EXAMPLE 9

A product according to the invention can be used as a preservative in an emulsion cream Thick Vaseline oil: 6 g.
mixture of cetostearyl alcohol and oxymethylene cetostearyl alcohol: 9 g.
anhydrous monosodium phosphate: 0.300 g.
Disodium Tetracemate: 0.010 g.
Vaseline 15 g.
CM 41075: 0.100 g.
phosphoric acid to pH 4.5.
purified water added to a total of: 100 g.

EXAMPLE 10

A product according to the invention can be used as a preservative in a cream for cosmetological use collagen: 0.500 g.
carboxypolymethylene 934: 0.400 g.
hydrogenated lanolin: 4 g.
perhydrosqualene: 20 g.
polyoxymethylated sorbitol monopalmitate: 2 g.
SR 42913: 0.150.
lactic acid or sodium hydroxide to pH 6.5.
purified water added to a total of: 100 g.

EXAMPLE 11

Foaming detergent liquid antiseptic preparation

CM 41075: 0.3 g.
alkyldimethylcarboxymethyalmine (30% solution): 15 g.
disodium tetracemate: 0.1 g.
propylene glycol: 20 g.
sodium hydroxide to pH 5.8.
purified water added to a total of: 100 g.

EXAMPLE 12

Foaming detergent liquid antiseptic preparation

SR 42913: 0.2 g.

sodium sulfonate paraffin: 15 g.

sodium hydroxide or lactic acid to pH 5.2.

purified water added to a total of: 100 g.

EXAMPLE 13

Disinfectant for inert surface

SR 41576: 0.5 g.

dodecyldimethylcarboxydimethylamine: 20 g.

disodium tetracemate: 2 g.

lactic acid to pH 3.5.

purified water added to a total of: 100 g.

EXAMPLE 14

Preservative for fruit juice or jam

SR 41576 micronized: 0.05%.

EXAMPLE 15

Preservative for creams

SR 42900 micronized: 0.05%.

We claim:

1. A method of preventing undesired activity due to bacteria or fungi comprising applying to a substrate or incorporating in a composition where such undesired bacterial or fungal activity is present or is likely to develop, comprising applying to said substrate or incorporating in said composition an effective amount of a benzoic acid derivative of formula

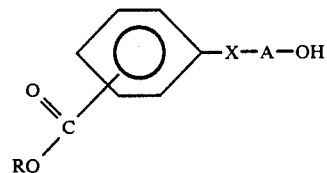

in which
    A represents a straight or branched alkyl group with 3 to 4 carbon atoms;
    X represents an oxygen atom or a direct bond;
    R represents hydrogen or an alkyl group with 2 to 6 carbon atoms, optionally substituted by an alcohol function;
or a therapeutically acceptable salt of said derivative, as a disinfectant active against bacteria and fungi.

2. A method of preventing undesired activity due to bacteria or fungi comprising applying to a substrate or incorporating in a composition where such undesired bacterial or fungal activity is present or is likely to develop, comprising applying to said substrate or incorporating in said composition an effective amount of a benzoic acid derivative of formula:

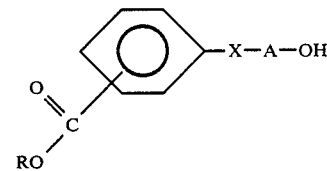

in which
    A represents a straight or branched alkyl group with 3 to 4 carbon atoms;
    X represents an oxygen atom or a direct bond;
    R represents hydrogen or an alkyl group with 2 to 6 carbon atoms, optionally substituted by an alcohol function;
or a therapeutically acceptable salt of said derivative, as a preservative agent, active against bacteria and fungi.

* * * * *